United States Patent
Korakianitis et al.

Patent Number: 5,980,473
Date of Patent: Nov. 9, 1999

[54] SURGICAL APPARATUS FOR DETERMINING LIGAMENT AND TENDON TENSION

[75] Inventors: Theodosios Korakianitis, Chesterfield; Jack Engsberg, Eureka; David E. Crawford, Jr., Des Peres, all of Mo.

[73] Assignee: Barnes-Jewish Hospital, St. Louis, Mo.

[21] Appl. No.: 09/056,262

[22] Filed: Apr. 7, 1998

Related U.S. Application Data

[60] Provisional application No. 60/042,819, Apr. 8, 1997.

[51] Int. Cl.$^6$ ................................................. A61B 5/103
[52] U.S. Cl. .................. 600/587; 73/862.07; 73/862.21; 606/148
[58] Field of Search ..................................... 600/587, 595, 600/592; 606/53, 139, 144, 148; 73/862.07, 862.21, 862.23, 862.42

[56] References Cited

U.S. PATENT DOCUMENTS

| | | | |
|---|---|---|---|
| 4,570,641 | 2/1986 | Lieber et al. | 600/587 |
| 4,702,431 | 10/1987 | Kaneko | 73/862.32 |
| 5,147,362 | 9/1992 | Goble | 606/72 |
| 5,213,112 | 5/1993 | Niwa et al. | 600/587 |
| 5,266,075 | 11/1993 | Clark et al. | 623/15 |
| 5,289,826 | 3/1994 | Kovacevic | 600/587 |
| 5,400,811 | 3/1995 | Meibauer | 132/322 |
| 5,496,336 | 3/1996 | Cosgrove et al. | 606/139 |
| 5,540,705 | 7/1996 | Meade et al. | 606/139 |
| 5,701,913 | 12/1997 | McPherson et al. | 600/587 |
| 5,871,036 | 2/1999 | Murayama et al. | 140/119 |

Primary Examiner—Max Hindenburg
Assistant Examiner—Charles Marmor, II
Attorney, Agent, or Firm—Senniger, Powers, Leavitt & Roedel

[57] ABSTRACT

Apparatus for applying a tensile force to a band of fibrous tissue of a patient. The apparatus includes a base for supporting the apparatus against a patient and a tensioning element moveably mounted on the base. The tensioning element is adapted for connection to a first end of the band of fibrous tissue of the patient so that movement of the element relative to the base moves the first end of the band relative to a second end of the band opposite the first end thereby to stretch the band and develop a tensile force in it. The tensile force developed in the band of fibrous tissue is a function of the movement of the tensioning element relative to the base.

11 Claims, 5 Drawing Sheets

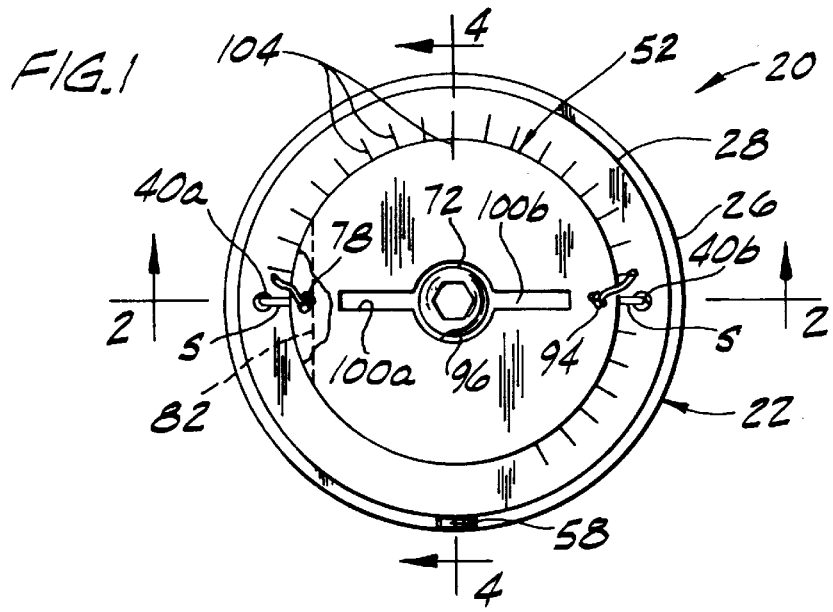
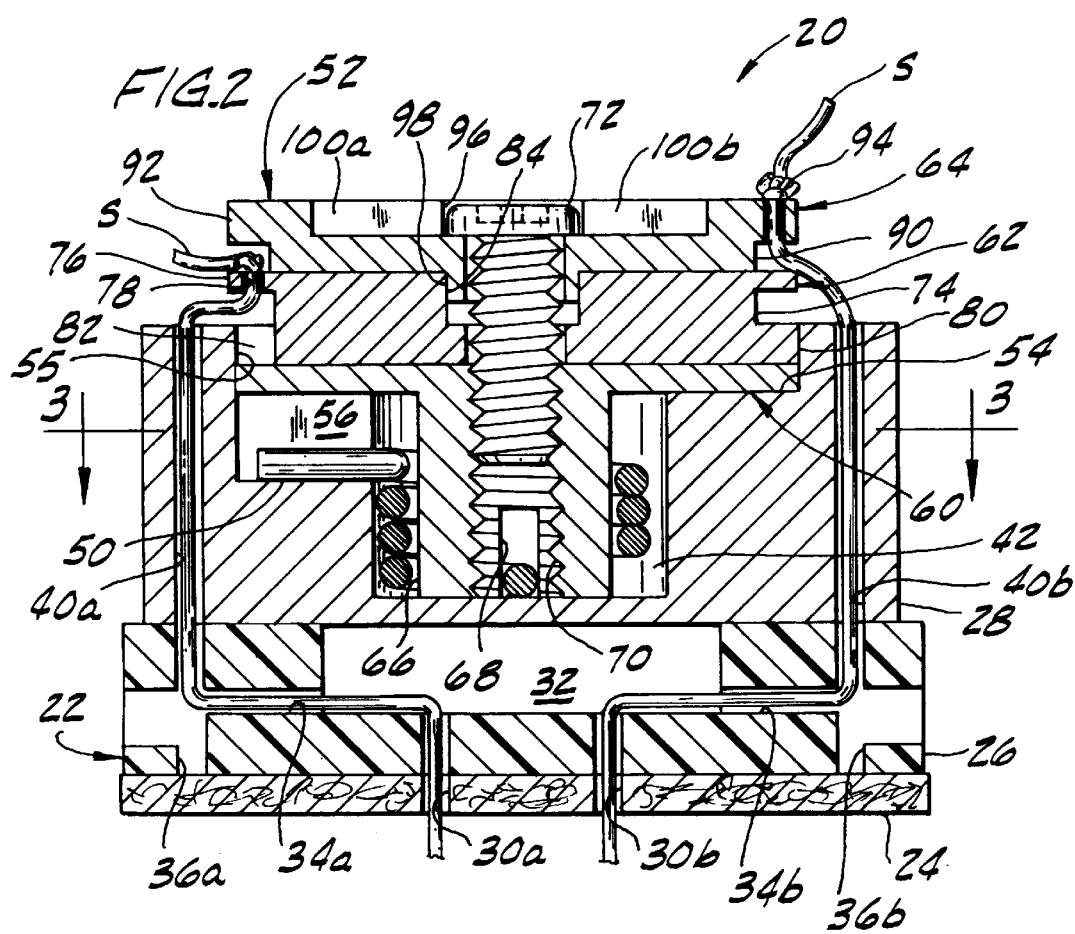

SURGICAL APPARATUS FOR DETERMINING LIGAMENT AND TENDON TENSION

This application claims benefit of Provisional Patent Application No. 60/042,819, filed Apr. 8, 1997, which is hereby incorporated by reference.

BACKGROUND OF THE INVENTION

This invention relates generally to apparatus for applying a tensile force to a band of fibrous tissue, such as a tendon or ligament of a patient, during surgery.

Surgeons move and/or change the length of tendons, ligaments and other bands of fibrous tissue associated with various joints of the body for many reasons. When surgeons perform these procedures, the specific tension in the band of fibrous tissue affects the outcome of the surgery.

For example, children with cerebral palsy (CP) commonly have an orthopedic problem known as equinus deformity in which their toes, rather than their heels, touch the ground at the beginning of each step. Heel cord transfer (HCT) surgery is used to correct or reduce this problem. During HCT surgery, the tendo achillis (i.e., the Achilles tendon) is removed from its insertion site on the calcaneum (i.e., the os calcis or heel bone) and repositioned at a location closer to the axis of the ankle joint. The surgery decreases the torque generating capacity of the gastrocnemius and soleus muscles (i.e., the calf muscles), thereby reducing the equinus position.

Two variables dictate the outcome of HCT surgery. The first is the position of the ankle when reattaching the tendon. The second is the tension in the tendon when it is reattached. For instance, if the foot is dorsiflexed (i.e., rotated upward) too much and/or too little tension is placed on the tendon as it is attached, then the patient may be unable to produce adequate plantarflexion torque (i.e., torque causing downward rotation of the foot). Although inadequate plantarflexion torque eliminates the equinus deformity, it also reduces the ability to push off the ground with the toes during the propulsive phase of gait, resulting in increased energy expenditure, slower gait speed, crouched gait and/or knee hyperextension.

Presently, tendon (and ligament) tension during HCT and other tendon and ligament transfers is based solely upon the experience of the surgeon and can vary widely. The resulting variation can lead to inconsistent results and can detrimentally affect the outcome of the surgery. In spite of the need for consistent results, the inventors are unaware of any clinical instruments for simultaneously setting and measuring tension in tendons and ligaments, and for periodically adjusting tension in tendons and ligaments. Further, because no instruments are used, few if any quantitative data have been recorded to evaluate the magnitudes, sensitivity, repeatability, and effectiveness of tendon and ligament transfer procedures.

SUMMARY OF THE INVENTION

Among the several objects and features of the present invention may be noted the provision of apparatus for applying a tensile force to a band of fibrous tissue of a patient; the provision of apparatus for determining the tensile force applied to a band of fibrous tissue; and the provision of such apparatus which can be used during surgery without interfering with the surgical procedure.

Briefly, apparatus of this invention is for applying a tensile force to a band of fibrous tissue of a patient. The apparatus comprises a base for supporting the apparatus against a patient and a tensioning element moveably mounted on the base. The tensioning element is adapted for connection to a first end of the band of fibrous tissue of the patient so that movement of the element relative to the base moves the first end of the band relative to a second end of the band opposite the first end thereby to stretch the band and develop a tensile force in it. The tensile force developed in the band of fibrous tissue is a function of the movement of the tensioning element relative to the base.

In another aspect of the invention, the apparatus comprises a base for supporting the apparatus against a patient, and a circular spool rotatably mounted on the base. The spool is adapted for receiving a suture connected to a first end of the band of fibrous tissue of the patient so that rotation of the spool relative to the base winds the suture around the spool and moves the first end of the band relative to a second end of the band opposite the first end thereby to stretch the band and develop a tensile force in it. The tensile force developed in the band of fibrous tissue is a function of the rotation of the spool relative to the base. The apparatus also comprises a torsional spring connected to the spool so that a first end of the spring is angularly displaced relative to a second end of the spring opposite the first end as the spool rotates relative to the base.

In yet another aspect of the invention, the apparatus comprises a base for supporting the apparatus against a patient and a circular spool rotatably mounted on the base. The spool is adapted for receiving a suture connected to a first end of the band of fibrous tissue of the patient so that rotation of the spool relative to the base winds the suture around the spool and moves the first end of the band relative to a second end of the band opposite the first end thereby to stretch the band and develop a tensile force in it. The apparatus also comprises a torque wrench connected to the spool for measuring a torque applied to the spool as the spool rotates relative to the base. The tensile force developed in the band of fibrous tissue is a function of the torque.

Other objects and features of the invention will be in part apparent and in part pointed out hereinafter.

BRIEF DESCRIPTION OF THE DRAWINGS

FIG. 1 is a top plan of a first embodiment of apparatus of the present invention for applying a tensile force to a band of fibrous tissue of a patient;

FIG. 2 is a cross section of the first embodiment of the apparatus taken in the plane of line 2—2 of FIG. 1;

Corresponding reference characters indicate corresponding parts throughout the several views of the drawings.

DETAILED DESCRIPTION OF THE PREFERRED EMBODIMENT

Figure 3:
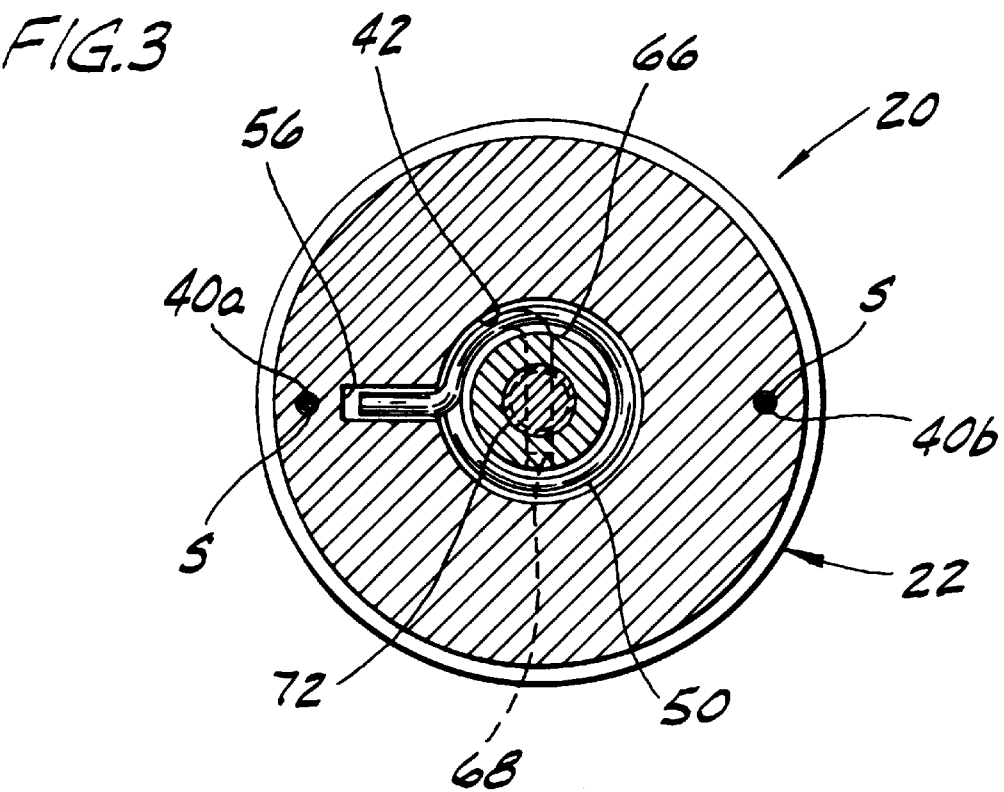
FIG. 3 is a cross section of the first embodiment of the apparatus taken in the plane of line 3—3 of FIG. 2.

Referring now to the drawings and in particular to FIG. 1, a first embodiment of apparatus for applying a tensile force to a band of fibrous tissue T, such as a muscle, ligament or tendon of a patient, during surgery is generally designated by the reference numeral 20. As illustrated in FIG. 2, the apparatus 20 comprises a base, generally designated 22, for supporting the apparatus against a patient. The base 22 of the preferred embodiment includes a felt pad 24 for cushioning the interface between the base and the patient, a Teflon® spacer 26 for maintaining the spacing between two ends of a suture S entering the base, and a cylindrical aluminum body 28. Teflon is a U.S. federally registered trademark of E.I. du Pont de Nemours and Company.

As further illustrated in FIG. 2, two holes 30a, 30b, extend through the spacer 26 for maintaining the ends of the suture S at a constant spacing so they do not rip the skin E (FIG. 6) of the patient. Although other spacings are envisioned as being within the scope of the present invention, the holes 30a, 30b of the preferred embodiment are approximately 8 mm apart. The holes 30a, 30b open into a cavity 32 formed in the spacer 26. A second set of holes 34a, 34b extends radially outward from the cavity 32 and a third set of holes 36a, 36b extends axially through the spacer 26 so they intersect the second set of holes. Although other spacings are envisioned as being within the scope of the present invention, the holes 36a, 36b of the preferred embodiment are approximately 28 mm apart. The spacer 26 of the preferred embodiment is made of Teflon® material to provide a low coefficient of friction so the suture S slides easily through the spacer. The edges of each of the holes 30a, 30b, 34a, 34b, 36a, 36b may be rounded to further reduce friction between the suture S and the spacer 26.

Figure 4:
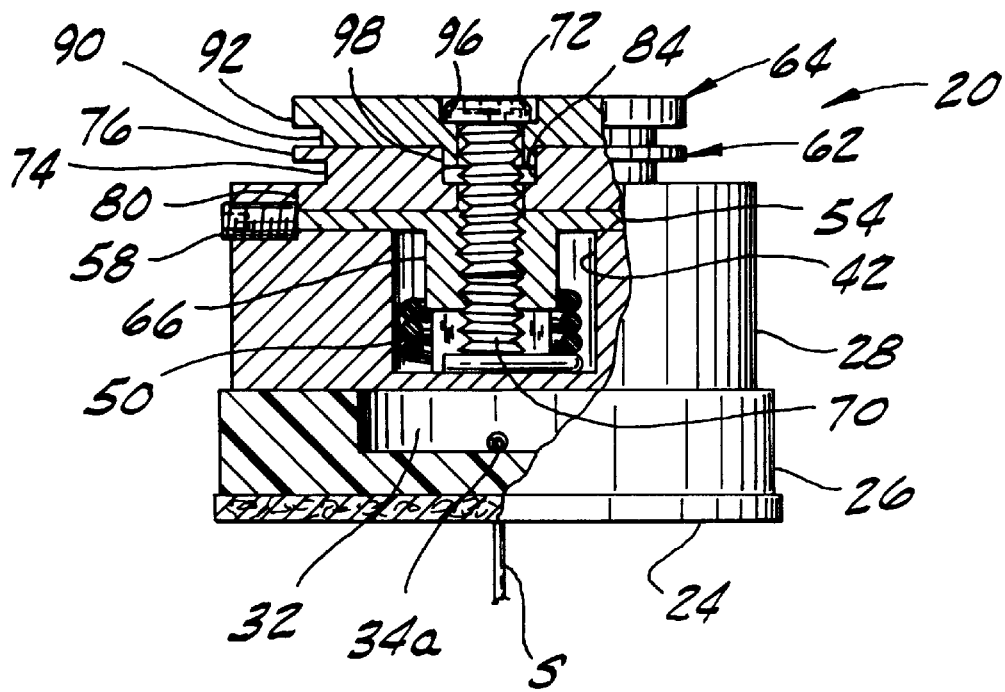
FIG. 4 is a cross section of the first embodiment of the apparatus taken in the plane of line 4—4 of FIG. 1.

As further illustrated in FIG. 2, two holes 40a, 40b extend axially through the body 28 at the same spacing as the third set of holes 36a, 36b in the spacer 26 (e.g., 28 mm). A cavity 42 formed in the body 28 receives a torsional spring 50 and a tensioning element or spool, generally designated by 52. The cavity 42 includes a shoulder 54 against which the spool 52 seats. The shoulder 54 is surrounded by a wall 55 which maintains concentricity between the spool 52 and the base 22. A slot 56 formed in the shoulder 54 retains one end of the spring 50 to prevent it from turning in the cavity 42. As illustrated in FIG. 3, this end of the spring 50 is bent outward and the other end is bent inward for engaging the spool 52 as will be explained below. The spring 50 is selected to have a torsional spring characteristic which develops a predetermined torque when its ends are rotated with respect to one another by a specified amount. For instance, the spring 50 may develop about 4.2 inch pounds of torque when one end of the spring is rotated 90° relative to the other end. As illustrated in FIG. 4, a set screw fastener 58 extends through a threaded hole in the body 28 for engaging the spool 52 to prevent it from rotating with respect to the base 22 once a desired tensile force is achieved in the band of fibrous tissue T.

The spool 52 comprises three spool elements, generally designated 60, 62, 64. The inner spool element 60 includes a stem 66 which extends through the torsional spring 50. A slot 68 formed in the end of the stem 66 receives the end of the torsional spring 50 which is bent inward. A threaded hole 70 extends axially through the inner element 60 for receiving a screw fastener 72 to prevent movement between the spool elements 60, 62, 64 once a desired angular relationship is achieved between them.

The middle spool element 62 has a circumferential groove 74 for receiving the suture S as it winds around the spool 52. A flange 76 defining the upper side of the groove 74 (as shown FIG. 2) has a hole 78 through which the end of the suture S is threaded before being knotted to attach the suture to the spool 52. A flange 80 defining the lower side of the groove 74 has a segment 82 missing under the hole 78 to permit access for threading the suture S through the hole. A counterbored hole 84 extends through the center of the middle element 62 for receiving the screw fastener 72.

The outer spool element 64 has a circumferential notch 90 for receiving the suture S as it winds around the spool 52. A flange 92 defining the upper side of the notch 90 as shown has a hole 94 through which the end of the suture S is threaded before being knotted to attach the suture to the spool 52. A counterbored hole 96 extends through the center of the outer element 64 for receiving the screw fastener 72 so its head is recessed. A rim 98 formed around the hole 96 in the outer element 64 has a close fit in the counterbored hole 84 in the middle element 62 to maintain concentricity of the middle and outer elements of the spool. As illustrated in FIG. 1, slots 100a, 100b are positioned on either side of the hole 98 for receiving a tool 102 (FIG. 6) to turn the spool 52 relative to the base 22 as will be explained below. Graduations or reference marks 104 on the upper surface(s) of the body 28 and/or outer spool element 64 indicate the relative angular relationship of the spool 52 to the base 22.

Figure 5A:
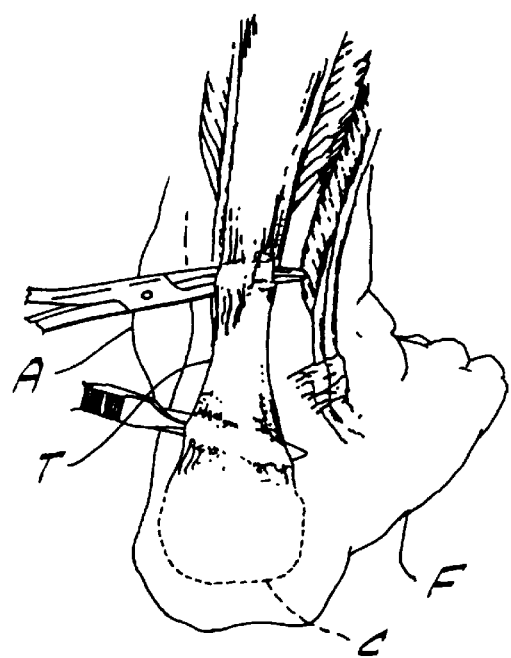
FIGS. 5a–5d are diagrams showing a heel cord transfer surgical procedure for correcting equinus deformity.
Figure 5B:
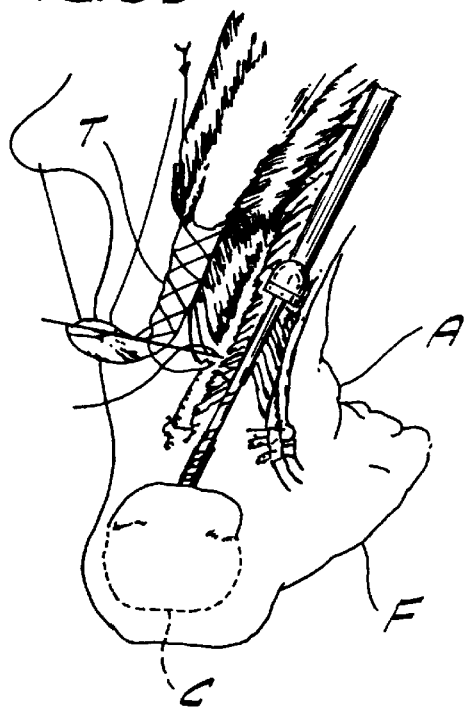
Figure 5C:
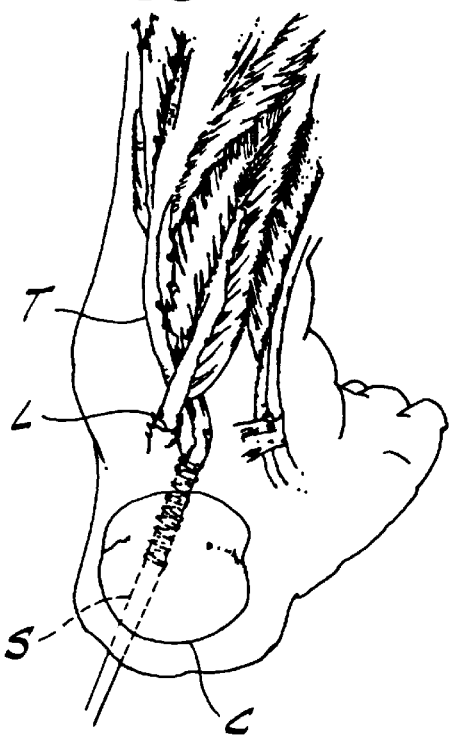
Figure 5D:
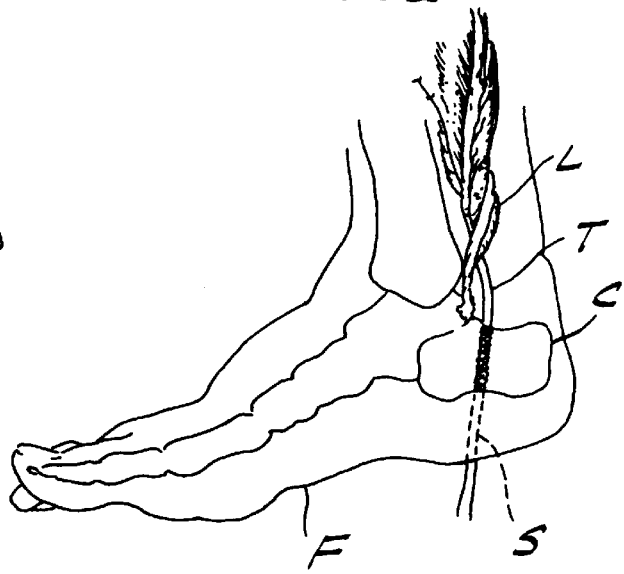

The apparatus 20 of the first embodiment is used to apply a tensile force to a band of fibrous tissue. For instance, as illustrated in FIGS. 5a–5d, apparatus 20 of the present invention may be used to perform HCT surgery. Referring to FIG. 5a, a surgeon makes an incision behind the ankle A of the patient to expose the Achilles tendon T. The tendon T is detached from the calcaneus C as near to the end of the tendon as possible. As illustrated in FIG. 5b, a hole is drilled through the calcaneus C just behind the surface which engages the astragalus bone (i.e., just behind the subtalar joint), and sutures S are attached to the end of the Achilles tendon T in a conventional manner. The sutures S are passed in front of the flexor longus hallucis muscle L from the inside of the leg toward the outside of the leg, as illustrated in FIGS. 5c and 5d, and through the hole drilled in the calcaneus C before being threaded through a hole made in the skin E at the heel of the foot F.

Figure 6:
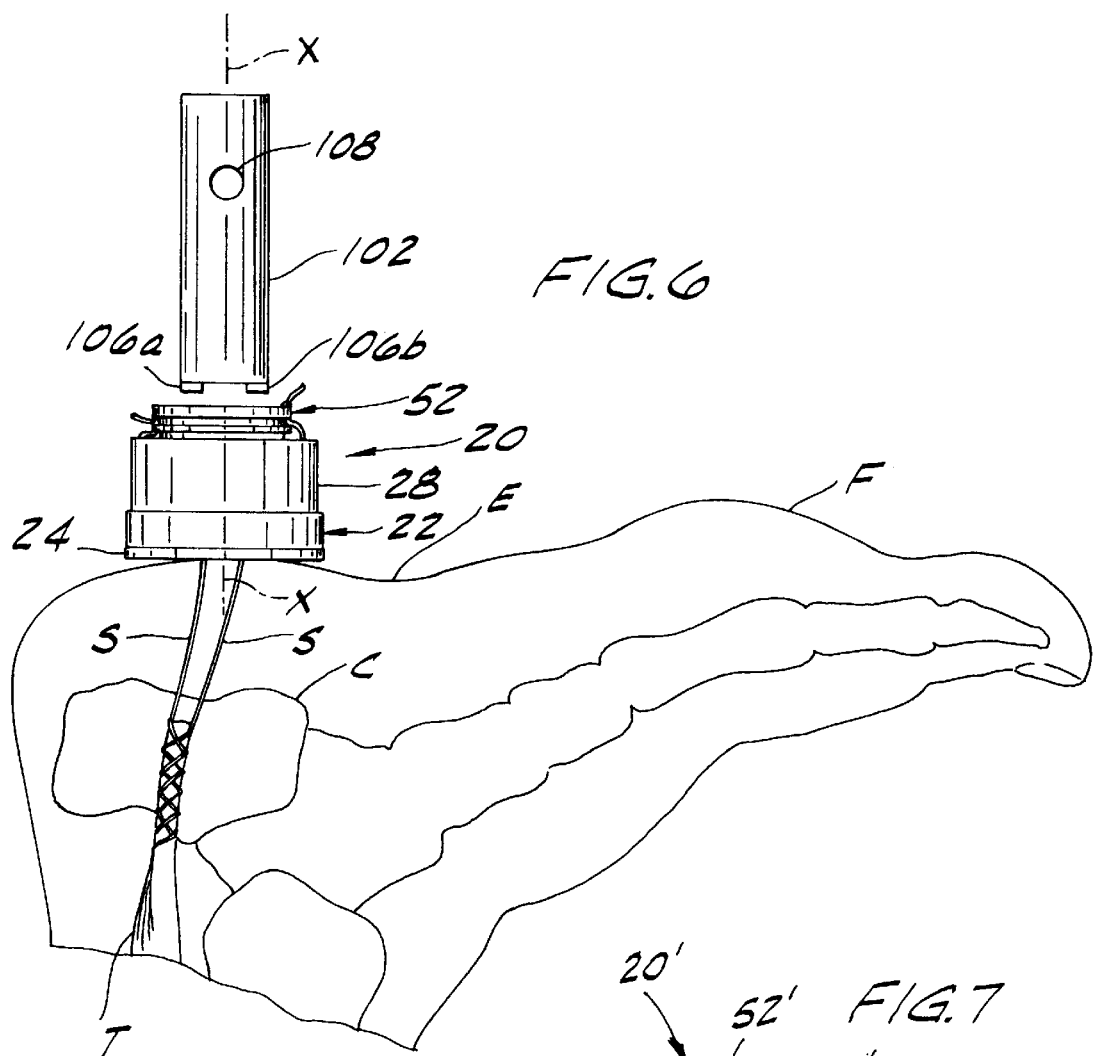
FIG. 6 is an elevation of the first embodiment of the apparatus shown applying a tensile force to an Achilles tendon.

As illustrated in FIG. 6, the sutures S are threaded through the felt pad 26 and then through the first two holes 30a, 30b in the base 22 of the apparatus 20. Next, the sutures S are threaded through the second and third sets of holes, 34a, 34b, 36a, 36b, respectively, in the base 22 and through the holes 40a, 40b in the body 28. One end of the suture S is threaded through the hole 78 in the middle element 62 and the other end of the suture is threaded through the hole 94 in the outer element 64. A non-slipping knot is tied in each end of the suture S close to the flanges 76, 92 of the middle and outer elements, 62, 64, respectively. The elements 60, 62, 64 of the spool 52 may be separated to perform the threading and knotting tasks described above by unscrewing the fastener 72. With the elements 60, 62, 64 loosely fastened together with the screw fastener 72, the middle and upper elements are turned clockwise as shown in FIG. 1 to take up slack in each end of the suture S. As will be apparent to those of ordinary skill in the art, because the middle and outer elements 62, 64, respectively, may be turned independently, they may be rotated different amounts to take up different amounts of slack in each end of the suture S. Once the slack is removed from each end of the suture S, the screw fastener 72 is tightened to fasten the spool elements 60, 62, 64 together so they do not turn relative to one another. In addition, as will be apparent to those skilled in the art, the inner and middle spool elements 60, 62, respectively, may be integrally formed without departing from the scope of the present invention.

As further illustrated in FIG. 6, the tool 102 has two blades 106a, 106b corresponding to the slots 100a, 100b (FIG. 1) in the outer element 64. The blades 106a, 106b are inserted in the slots 100a, 100b and the handle 108 of the tool 102 is used to rotate the spool 52 relative to the base 22 about an axis X which is generally parallel to the tissue T. As the spool 52 rotates, the ends of the suture S wrap around the spool equal amounts, thereby stretching the band of fibrous tissue T attached to the spool by the suture. As the tissue T stretches, a tensile force develops in it. The tensile force in the tissue T and in each end of the suture S varies as a function of the angular displacement between the spool 52 and base 22. The surgeon must overcome the resistance of the spring 50 in addition to that of the tissue T when turning the spool 62 with respect to the base 22. This gives the surgeon tactile feedback regarding the tensile force in the tissue and reduces the chance of over-stressing the tissue. Once the desired tensile force is achieved, the screw fastener 58 may be tightened to hold the spool 52 in place relative to the base 22, thereby maintaining the tensile force. The tissue may then be reattached to the bone and/or isolated so that movement is restricted for a period sufficient to permit the tissue to further reattach to the bone. The tensile force in the tissue T may be periodically checked and adjusted as necessary by loosening the fastener 58 and turning the spool 52 relative to the base. Alternatively, the tissue T may be secured to the bone with an attachment means such as a biodegradable screw (not shown) once the desired tension is achieved, and the apparatus 20 may be removed.

The tensile force developed in the tissue T when the spool 52 is rotated relative to the base 22 by a given angular displacement will vary from patient to patient and from tissue to tissue within a patient. However, it is envisioned that a statistical evaluation of tissues may be made so that the tensile force developed in the tissue of a particular patient may be estimated solely from the angular displacement induced between the spool 52 and the base 22. For instance, it might be determined that a tensile force of about 10 pounds may be achieved in an Achilles tendon of a patient by turning the spool 52 90° with respect to the base 22. Further, this estimate might be refined by taking into account various factors such as the size or age of the patient. Moreover, in the case of an Achilles tendon, the tissue T may have a stiffness several orders of magnitude greater than the stiffness of the spring 50. Thus, the angular displacement of the spring 50 gives an accurate measurement of the tensile force developed in the tendon, and statistical evaluation is unnecessary.

As will be apparent to those skilled in art, the spring 50 may be omitted or exchanged with springs having different spring characteristics depending upon the desired angular displacement to torque relationship. Further, the configuration of the apparatus may be changed so the relative displacement of the ends of the spring are not affected by the stiffness of the tissue being stretched. Still further, the configuration of the apparatus may be altered to permit the spring to be pretensioned so that it rotates the spool 52 relative to the base and applies the tensile force to the tissue.

Figure 7:
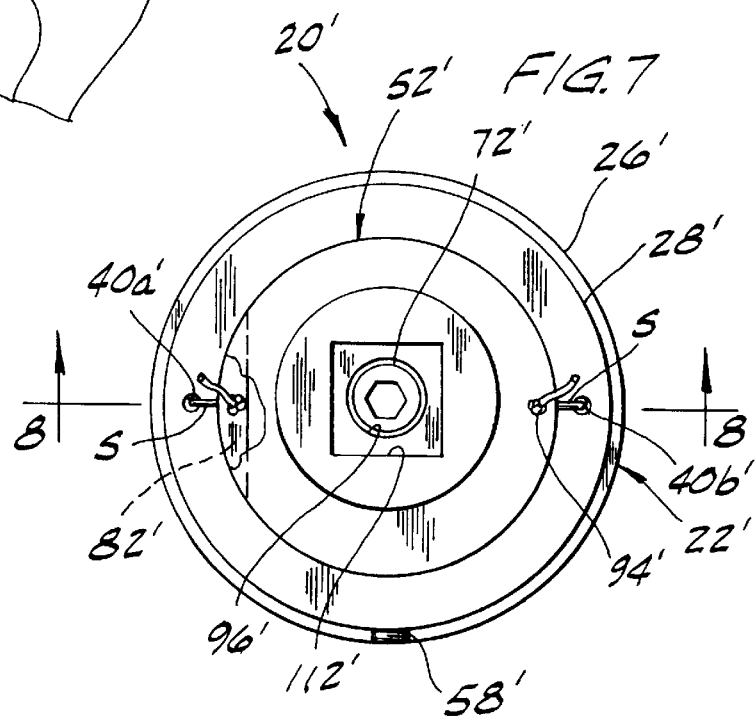
FIG. 7 is a top plan of a second embodiment of apparatus of the present invention for applying a tensile force to a band of fibrous tissue of a patient.
Figure 8:
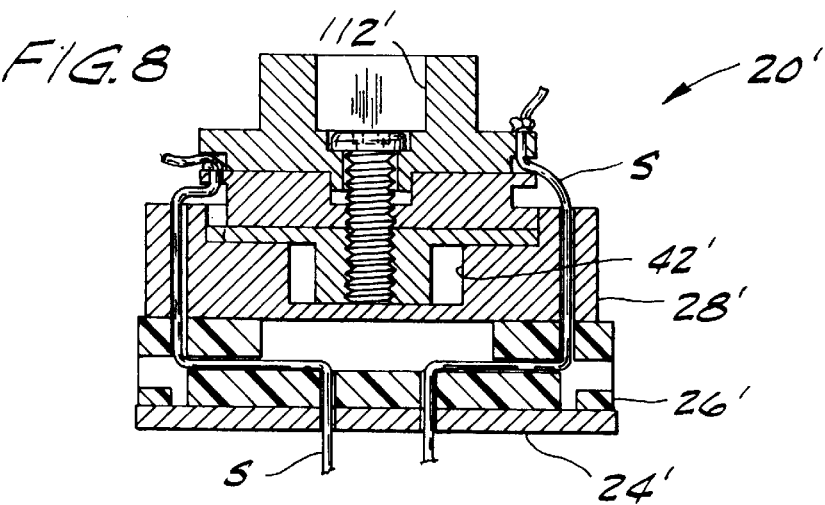
FIG. 8 is a cross section of the second embodiment of the apparatus taken in the plane of line 8—8 of FIG. 7.
Figure 9:
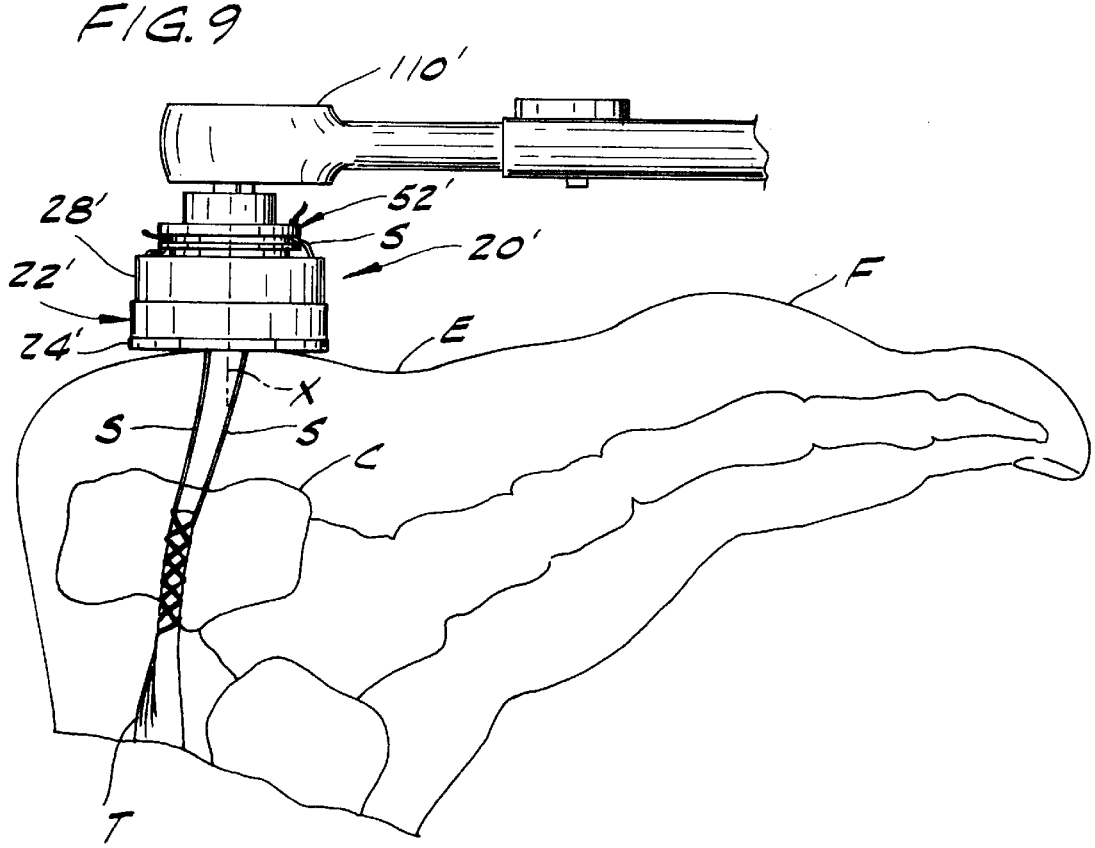
FIG. 9 is an elevation of the second embodiment of the apparatus shown applying a tensile force to an Achilles tendon.

A second preferred embodiment of apparatus 20' of the present invention is illustrated in FIGS. 7 and 8. In the second preferred embodiment, the spring is omitted and the apparatus is configured for use in combination with a conventional torque wrench 110'. The configuration of this embodiment is similar to the first. Elements of the second embodiment which are similar to those of the first embodiment will be identified with a prime symbol following the reference number. The body 28' is shorter than the body 28 of the first embodiment to reduce the overall height of the apparatus 20'. Moreover, the slots in the outer element 64 are replaced with a square drive socket 112' which accepts the square drive of the torque wrench 110'. As will be apparent to those of ordinary skill in the art, the apparatus 20' of the second embodiment is used similarly to the apparatus 20 of the first embodiment. However, rather than using a tool 102 to turn the spool 52', the torque wrench 110' is used. Further, as will apparent to those of ordinary skill in the art, the torque reading from the torque wrench 110' may be multiplied by a fixed conversion factor to determine the exact amount of tensile force developed in the tissue T.

Although the description presented above relates to determining the tensile force developed in an Achilles tendon, it will be understood by those of ordinary skill in the art that other embodiments may be adapted for developing and determining the tensile force in other bands of fibrous tissue throughout the body. For instance, the apparatus may be modified for use in ligament reconstruction at the knee, other tendon transfers at the ankle, and tendon transfers at the knee, hip, and wrist. In addition, although the description is directed to apparatus for use on the human body, it should be understood that apparatus for performing similar surgeries on nonhuman animals are within the scope of the present invention. Still further, the apparatus may be modified to apply torques, rather than tensile forces, to bands of tissue.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. Apparatus for applying a tensile force to a band of fibrous tissue of a patient, the apparatus comprising:

a base for supporting the apparatus against a patient; and a tensioning element moveably mounted on the base and adapted for connection to a first end of the band of fibrous tissue of the patient so that movement of the element relative to the base moves said first end of the band relative to a second end of the band opposite said first end of the band thereby to stretch the band and develop a tensile force therein, the tensile force developed in the band of fibrous tissue being a function of the movement of the tensioning element relative to the base.

2. Apparatus as set forth in claim 1 wherein said tensioning element is a circular spool rotatably mounted on the base such that the tensile force developed in the band of fibrous tissue is a function of angular displacement between the spool and base.

3. Apparatus as set forth in claim 2 wherein said spool rotates about an axis which is generally parallel to the band of fibrous tissue.

4. Apparatus as set forth in claim 2 further comprising a torsional spring connected to the spool so that a first end of the spring is angularly displaced relative to a second end of the spring opposite said first end of the spring as the spool rotates relative to the base.

5. Apparatus as set forth in claim 2 in combination with a torque wrench for measuring a torque applied to the spool as the spool rotates relative to the base, the tensile force developed in the band of fibrous tissue being a function of said torque.

6. Apparatus as set forth in claim 2 wherein the spool comprises at least two spool elements, one of said elements being adapted for receiving a first end of a suture connected to the band of tissue and another of said elements being adapted for receiving a second end of the suture opposite said first end of the suture, said spool elements being independently rotatable for removing different amounts of slack from each of said ends of the suture.

7. Apparatus as set forth in claim 1 wherein at least one of said base and tensioning element includes a scale for quantifying the tensile force developed in the band of fibrous tissue.

8. Apparatus as set forth in claim 1 further comprising a device for preventing movement between the tensioning element and the base to maintain a fixed tensile force in the band of fibrous tissue.

9. Apparatus for applying a tensile force to a band of fibrous tissue of a patient, the apparatus comprising:

a base for supporting the apparatus against a patient;

a circular spool rotatably mounted on the base and adapted for receiving a suture connected to a first end of the band of fibrous tissue of the patient so that rotation of the spool relative to the base winds the suture around the spool and moves said first end of the band relative to a second end of the band opposite said first end of the band thereby to stretch the band and develop a tensile force therein, the tensile force developed in the band of fibrous tissue being a function of the rotation of the spool relative to the base; and a torsional spring connected to the spool so that a first end of the spring is angularly displaced relative to a second end of the spring opposite said first end of the spring as the spool rotates relative to the base.

10. Apparatus as set forth in claim 9 wherein the spring has a spring characteristic selected so that the tensile force developed in the band of fibrous tissue equals a predetermined amount when the spool rotates a preselected amount relative to the base.

11. Apparatus for applying a tensile force to a band of fibrous tissue of a patient, the apparatus comprising:

a base for supporting the apparatus against a patient;

a circular spool rotatably mounted on the base and adapted for receiving a suture connected to a first end of the band of fibrous tissue of the patient so that rotation of the spool relative to the base winds the suture around the spool and moves said first end of the band relative to a second end of the band opposite said first end of the band thereby to stretch the band and develop a tensile force therein; and a torque wrench connected to the spool for measuring a torque applied to the spool as the spool rotates relative to the base, the tensile force developed in the band of fibrous tissue being a function of said torque.

* * * * *